United States Patent [19]

Sartorelli et al.

[11] Patent Number: 5,256,820
[45] Date of Patent: Oct. 26, 1993

[54] 1-ALKYL-2-ACYL-1,2-DISULFONYLHYDRAZINES

[75] Inventors: Alan C. Sartorelli, Woodbridge; Krishnamurthy Shyam, Hamden; Philip G. Penketh, New Haven, all of Conn.

[73] Assignee: Yale University, New Haven, Conn.

[21] Appl. No.: 790,689

[22] Filed: Nov. 8, 1991

[51] Int. Cl.$^5$ ............... C07C 311/02; C07C 311/14; C07C 311/15; A61K 31/18
[52] U.S. Cl. ........................................... 564/81
[58] Field of Search ............... 564/81; 514/601, 602, 514/604, 605

[56] References Cited

U.S. PATENT DOCUMENTS

| | | | |
|---|---|---|---|
| 4,684,747 | 8/1987 | Sartorelli et al. | 564/81 |
| 4,849,563 | 7/1989 | Sartorelli et al. | 514/155 |
| 4,892,887 | 1/1990 | Sartorelli et al. | 514/601 |
| 5,101,072 | 3/1992 | Sartorelli et al. | 564/81 |

OTHER PUBLICATIONS

Shyam et al., "Synthesis and Evaluation of 1,2,2-Tris(-sulfonyl)hydrazines as Antineoplastic and trypanocidal Agents", *J. Med. Chem.*, 30:2157–2161 (1987).
Shyam et al., J. Med. Chem. 33:2259–2264, 1990.
Penketh et al., J. Med. Chem. 33:730–732, 1990.
Shyam et al., J. Med. Chem. 30:2157–2161, 1987.
Shyam et al., J. Med. Chem. 29:1323–1325, 1986.
Shyam et al., J. Med. Chem. 28:525–527, 1985.

*Primary Examiner*—Allen J. Robinson
*Assistant Examiner*—P. O'Sullivan
*Attorney, Agent, or Firm*—Fish & Richardson

[57] ABSTRACT

Novel antineoplastic 1-alkyl-2-acyl-1,2-disulfonylhydrazine having the following formula and methods of therapy using those antineoplastic compounds:

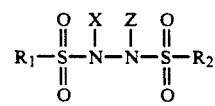

where $R_1$ and $R_2$ are (independently) alkyl, cycloalkyl, aryl, aralkyl or heteroaryl. X is an acyl group, and Z is an alkyl or a haloalkyl group.

14 Claims, No Drawings

1-ALKYL-2-ACYL-1,2-DISULFONYLHYDRAZINES

This research was supported in part by a U.S. Public Health Service grant (CA-02817) from the National Cancer Institute. The U.S. Government has certain rights in this invention.

FIELD OF THE INVENTION

This invention generally concerns compounds having antineoplastic activity and methods of therapy using these compounds.

BACKGROUND

One strategy for controlling tumors is to administer agents that alkylate cellular structures. Procarbazine, streptozotocin, and dacarbazine are examples of antineoplastic agents of this type.

Our co-owned U.S. Pat. Nos. (4,684,747; 4,849,563; and 4,892,887) disclose certain antineoplastic hydrazines with alkylating ability. Specifically, our '747 and '887 Patents disclose N,N'-bis(sulfonyl)hydrazines having methyl or chloroethyl substituents on the hydrazine moiety, as contrasted with N,N'-bis(sulfonyl)hydrazines having no alkyl substituent on the hydrazine moiety. The methyl or chloroethyl substituent is said to be essential for the generation of the reactive species necessary for antineoplastic activity.

We have published other studies on alkylating N,N'-bis(sulfonyl)hydrazines. See, Shyam et al. (1985) *J. Med. Chem.* 28:525–527; Shyam et al. (1986) *J. Med. Chem.* 29:1323–1325; Shyam et al. (1987) *J. Med. Chem.* 30:2157–2161; Penketh et al. (1990) *J. Med. Chem.* 33:730–732. In particular, Shyam et al. *J. Med. Chem.* (1990) 33:2259–2264 disclose certain tris(sulfonyl)hydrazines having antineoplastic activity. Specifically, 1-(2-chloroethyl)-1,2,2-tris(methylsulfonyl)hydrazine displays potent antineoplastic activity. 1-Methyl-1,2,2-tris(methylsulfonyl)hydrazine also showed antineoplastic activity and was relatively less toxic.

SUMMARY OF THE INVENTION

One aspect of the invention features 1-alkyl-2-acyl-1,2-disulfonylhydrazines having the formula:

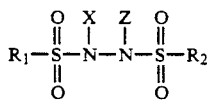

where $R_1$ and $R_2$ are (independently) alkyl, cycloalkyl, aryl, aralkyl or heteroaryl. X is an acyl group, and Z is an alkyl or a haloalkyl group.

Preferably X is

where $R_3 = -CH_3$, $-C_2H_5$, n-$C_3H_7$, t-$C(CH_3)_3$, $-CH_2-O-CH_3$, or $-C_6H_5$. Also, preferably Z is a lower (less than $C_5$) alkyl group or a halosubstituted alkyl group (most preferably Z is a methyl or chloroethyl group). Also, preferably $R_1$ and $R_2$ are methyl.

In a second aspect, the invention features methods for controlling neoplastic cell growth by administering the compounds described herein to the cells. Preferably, the method features administering the compounds in vivo to a human patient. The invention includes administering the compounds to non-human mammals or to control growth of cultured cells.

The above-described compounds are designed to be relatively stable, yet to yield an alkylating agent at an optimum (rather than a slow) rate of generation. Without wishing to bind ourselves to any particular mechanism, we believe the compounds are prodrugs which yield the alkylating agent by hydrolysis of the N-acyl bond. That bond is more prone to enzyme mediated hydrolytic cleavage than the N-sulfonyl bond (the corresponding bond of the tris(sulfonyl)hydrazines described in the Background, above). Also, hydrolytic removal of the acyl group gives a relatively higher yield of the alkylating species than cleavage of the corresponding sulfonyl group. Additionally, the N-acyl bond resembles a peptide linkage and may be prone to hydrolytic cleavage (a particularly effective strategy for targeting metastatic tumors that reportedly have relatively high levels of proteases; see Ruddon, *Cancer Biology*, Second Edition, Oxford University Press, New York 1987, pp. 446–448).

The compounds of the invention are expected to be relatively less toxic, permitting high enough doses to control neoplastic growth.

The lower acyl homologues are more water soluble and more potent, properties which assist in formulating therapeutic compositions.

The compounds are generally stable and resistant to spontaneous hydrolysis in aqueous media under neutral conditions at room temperature. Their serum half-lives can be controlled by controlling the nature of the acyl group.

The compounds may undergo protease- and thiol-mediated activation (as described in greater detail below), properties which improve targeting and counteract drug resistance.

Other features and advantages of the invention will be apparent from the following description of the preferred embodiments and from the claims.

DESCRIPTION OF THE PREFERRED EMBODIMENT

As outlined above, compounds of the invention are precursors of alkylating N,N'-bis(sulfonyl)hydrazines. The alkylating species is generated by deacylation. The alkyl group which ultimately is transferred to a biological molecule is attached to one of the hydrazine nitrogens. The preferred alkyl groups are listed above. Other haloalkyl groups such as 2-fluoroethyl and 2bromoethyl may be substituted without deviating from the spirit of the invention.

The preferred acyl groups are listed above. Other acyl groups may be substituted without deviating from the spirit of the invention.

Those skilled in the art will recognize that candidate compounds according to the invention can be tested for their ability to inhibit tumors such as the L1210 leukemia by the method described below.

The compounds according to the invention may be synthesized as follows. The corresponding 1,2-disulfonyl-1-alkylhydrazine 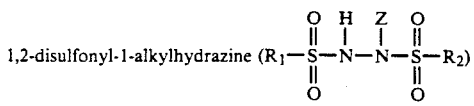

is reacted with the appropriate acyl chloride or acid anhydride, such as

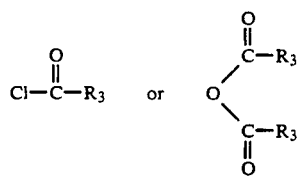

in a solvent such as acetone or acetonitrile in the presence of a base such as triethylamine. For example, the 1,2-disulfonyl-1-alkylhydrazine starting materials are obtained as described in Shyam et al. (1990), cited above, and in our '747/'887 Patents, hereby incorporated by reference. The starting material and the appropriate acid anhydride or acyl chloride are reacted by mixing the reactants in dry solvent and adding triethylamine dropwise at room temperature. After filtering the reaction mixture, the filtrate is evaporated to dryness. The residue is taken up in a solvent such as ethyl acetate and washed with dilute acid (e.g., HCl) and water. The ethyl acetate layer is dried and filtered. The filtrate is evaporated and the residue recrystallized from a suitable solvent or solvent mixture, e.g., ethanol or ethanol-petroleum ether.

The compounds of the invention, produced and purified as described above, have been found to be alkylating agents having antineoplastic activity in mice bearing the L1210 leukemia and B16 melanoma—i.e., they exhibit pronounced antitumor activity.

The compounds of this invention are preferably administered internally, e.g., intravenously, in the form of conventional pharmaceutical preparations, for example in conventional enteral or parenteral pharmaceutically acceptable excipients containing organic and/or inorganic inert carriers, such as water, gelatin, lactose, starch, magnesium stearate, talc, plant oils, gums, alcohol, Vaseline, or the like. The pharmaceutical preparations can be in conventional solid forms, for example, tablets, dragees, suppositories, capsules, or the like, or conventional liquid forms, such as suspensions, emulsions, or the like. If desired, they can be sterilized and/or contain conventional pharmaceutical adjuvants, such as preservatives, stabilizing agents, wetting agents, emulsifying agents, buffers, or salts used for the adjustment of osmotic pressure. The pharmaceutical preparations may also contain other therapeutically active materials.

The pharmaceutical preparation should include an amount of a compound of this invention effective for antineoplastic activity. The effective dosage will depend on the antineoplastic activity and toxicity of the particular compound employed and is thus within the ordinary skill of the art to determine for any particular host mammal or other host organism. Suitable dosages may be, for example, in the range of about 1–15 mg per kg for man.

Alternatively, the claimed compounds may be used to control proliferation of neoplastic cells, in vitro, or they may be used as antineoplastic agents in (non-human) mammals.

The following examples are provided to illustrate the invention, but not to limit its scope.

EXAMPLE 1

1-Acetyl-1,2-bis(methylsulfonyl)-2-(2-chloroethyl)-hydrazine. To a stirred solution of 1,2-bis(methylsulfonyl)-1-(2-chloroethyl)hydrazine (1.5 g, 0.006 mol) and acetic anhydride (4.3 g, 0.042 mol) in dry acetone (50 mL), triethylamine (3.6 g, 0.035 mol) was added dropwise at room temperature. After an additional 16 h, the reaction mixture was evaporated to dryness. The residue was taken up in ethyl acetate (50 mL) and washed with dilute hydrochloric acid (3×10 mL), followed by water (3×10 mL). The ethyl acetate layer was dried over anhydrous magnesium sulfate, treated with charcoal and filtered. On evaporation of the solvent a solid was obtained which, on recrystallization from ethanol, gave 1.1 g (62.8%) of the title compound: mp 148°–149° C.; $^1$H NMR (acetone-$d_6$) $\delta$ 3.8–4.2 (m, 4 H, $CH_2CH_2$), 3.5 and 3.3 (2 s, 6 H, $2CH_3SO_2$), 2.4 (s, 3 H, $CH_3CO$). Anal. ($C_6H_{13}ClN_2O_5S_2$) C, H, N.

EXAMPLE 2

1,2-Bis(methylsulfonyl)-1-(2-chloroethyl)-2-propionylhydrazine. To a stirred solution of 1,2-bis(methylsulfonyl)-1-(2-chloroethyl)hydrazine (1.25 g, 0.005 mol) and propionyl chloride (3.20 g, 0.035 mol) in dry acetone (20 mL), triethylamine (0.014 mol) was added dropwise at room temperature. A precipitate was formed immediately. After an additional 20 h, the reaction mixture was filtered and the filtrate evaporated in dryness in vacuo. The residue was taken up in ethyl acetate (100 mL) and washed with dilute hydrochloric acid (3×15 mL), followed by water (2×10 mL). The ethyl acetate layer was dried over anhydrous magnesium sulfate, filtered and the filtrate evaporated to dryness in vacuo. The residue was triturated with petroleum ether to give a solid which, on recrystallization from absolute ethanol, afforded 0.71 g (46.4%) of the title compound: mp 97°–98° C.; $^1$H NMR (acetone-$d_6$) $\delta$ 3.8–4.2 (m, 4 H, $CH_2CH_2$), 3.5 and 3.3 (2 s, 6 H, 2 $CH_3SO_2$), 2.8 (q, 2 H, $COCH_2$), 1.1 (t, 3 H, $COCCH_3$). Anal. ($C_7H_{15}ClN_2O_5S_2$) C, H, N.

The compounds of Examples 3–6 were synthesized by using procedures similar to the one described above for Example 2.

EXAMPLE 3

1,2-Bis(methylsulfonyl)-1-(n-butyryl)-2-(2-chloroethyl)hydrazine. This compound was recrystallized from ethanol-petroleum ether: yield, 59.4%; mp 68°–69° C.; $^1$H NMR (acetone-$d_6$) $\delta$ 3.8–4.2 (m, 4 H, $CH_2CH_2Cl$), 3.5 and 3.3 (2 s, 6 H, 2 $CH_3SO_2$), 2.8 (t, 2 H, $COCH_2$), 1.6 (m, 2 H, $COCCH_2C$), 1.0 (t, 3 H, $CCH_3$). Anal. ($C_8H_{17}ClN_2O_5S_2$) C, H, N.

EXAMPLE 4

1,2-Bis(methylsulfonyl)-1-(2-chloroethyl)-2-pivaloyl-hydrazine. This compound was recrystallized from ethanol: yield, 4.6%; mp 115°–116° C.; $^1$H NMR (acetone-$d_6$) $\delta$ 3.9–4.2 (m, 4 H, $CH_2CH_2Cl$), 3.5 and 3.4 (2 s, 6 H, 2 $CH_3SO_2$), 1.4 [s, 9 H, $C(CH_3)_3$]. Anal. ($C_9H_{19}ClN_2O_5S_2$) C, H, N.

EXAMPLE 5

1,2-Bis(methylsulfonyl)-1-(2-chloroethyl)-2-methoxyacetylhydrazine. This compound was recrystallized from ethanol: yield, 77.7%; mp 99°–100° C.; $^1$H NMR (acetone-$d_6$) $\delta$ 4.5 (d, 2 H, $COCH_2$), 3.8–4.3 (m, 4 H, $CH_2CH_2$), 3.6 (s, 3 H, $OCH_3$), 3.5 and 3.4 (2 s, 6 H, 2 $CH_3SO_2$) Anal. ($C_7H_{15}ClN_2O_6S_2$) C, H, N.

EXAMPLE 6

1-Benzoyl-1,2-bis(methylsulfonyl)-2-(2-chloroethyl)-hydrazine. This compound was recrystallized from ethanol: yield, 53.5%; mp 106°–107° C. $^1$H NMR (acetone-d$_6$) δ 7.5–7.9 (m, 5 H, aromatic H), 4.0 and 3.7 (2 t, 4 H, CH$_2$CH$_2$), 3.6 and 3.2 (2 s, 6 H, 2 CH$_3$). Anal. (C$_{11}$H$_{15}$ClN$_2$O$_6$S$_2$)C, H, N.

EXAMPLES 7–12

The antineoplastic activity of each of the compounds of Examples 1–6 was assessed by measuring their effects on the survival time of mice bearing the L1210 leukemia by the method generally disclosed in Shyam et al. *J. Med. Chem.* (1990) 33:2259–2264. The compounds were administered once daily for six consecutive days. Percent change in body weight from onset to termination of therapy was recorded. The results are summarized in Table I. All of the compounds tested produced at least partial 60-day "cures" of mice bearing the L1210 leukemia. Furthermore, the most water-soluble analogs of this class, i.e., compounds of Examples 1, 2, and 5, produced their curative effects at relatively low dosage levels. Thus, the acetyl derivative (Example 1) was highly active against the L1210 leukemia, producing 80% 60-day "cures" of tumor-bearing mice at 7.5 mg/kg administered as six daily intraperitoneal doses. However, the propionyl analog (Example 2) appeared to be the most potent, producing 60% "cures" of mice bearing the L1210 leukemia at 5 mg/kg×6. This compound also produced 80–90% "cures" at 10 and 15 mg/kg×6. The methoxyacetyl analog (Example 5), on the other hand, produced 100% "cures" of tumor-bearing mice at 10 mg/kg×6 but was lethal at the higher dose levels examined.

TABLE I

Effects of 2-Acyl-1,2-bis(methylsulfonyl)-1-(2-chloroethyl)hydrazines on the Survival Time of Mice Bearing the L1210 Leukemia

| Compd | Opt. effective daily dose, mg/kg[a,b] | AvΔ wt %[c] | % T/C[d] | % 60-day survivors |
|---|---|---|---|---|
| PRIOR ART[e] | 60 | −7.2 | — | 100 |
| 1 | 7.5 | +1.0 | 341 | 80 |
| 2 | 10 | −6.4 | 217 | 90 |
| 3 | 10 | 0.0 | 207 | 20 |
| 4 | 20 | 0.0 | 302 | 60 |
| 5 | 10 | −8.4 | — | 100 |
| 6 | 20 | −7.7 | 160 | 20 |

[a]Administered once daily for six consecutive days, beginning 24 h after tumor implantation, with 5–10 mice being used per group.
[b]Average day of death for untreated tumor-bearing mice was 8.4.
[c]Average percent change in body weight from onset to termination of therapy. Average percent change in body weight for vehicle-treated controls was +2.0.
[d]% T/C = average survival time of treated/control mice × 100; 60-day survivors are listed separately and are not included in this calculation.
[e]The prior art compound used for comparison was 1-(2-chloroethyl)-1,2,2-tris(methylsulfonyl)hydrazine.

EXAMPLE 13

The compounds of the invention are relatively stable. As a measure of their stability, spontaneous decomposition in aqueous media was measured in phosphate buffer, pH 7.4 (37° C.). Hydrolysis at N-1 would result in the generation of a carboxylic acid and the corresponding 1,2-bis(methylsulfonyl)-1-(2-chloroethyl)hydrazine. Since both of these compounds are ionized under these conditions, the release of protons can be used to follow the decomposition of these and related compounds. The release of protons can be assayed by following the decrease in absorbance at 560 nm of a weakly buffered (1 mM potassium phosphate) phenol red (21 mg/L) solution. The assay has been calibrated using HCl standards. Compounds of examples 1–6 were essentially stable under these conditions. The spontaneous hydrolysis of the compound of Example 1 at pH 7.4, 37° C. in 1 mM phosphate buffer occurs at approximately 0.7% of the rate of the corresponding prior art compounds [1,2,2-tris(methylsulfonyl)-1-(2-chloroethyl)hydrazine] under the same conditions. The rate of hydrolysis was highly sensitive to changes in temperature and pH (Tables II and III). The rate was found to double for every 5° C. rise in temperature and increased approximately 50% for every 0.2 unit rise in pH (in the pH 7.4–7.8 range). At pH 7.4, 37° C., a 200 μM solution of the compound of Example 1 hydrolyzes at the rate of approximately 0.6% per hour. This rate could be appreciably decreased by slight acidification and/or storage at low temperatures. Therefore, stable aqueous solutions of this agent can be formulated. The other analogs synthesized according to Examples 2–6 also hydrolyzed at relatively slow rates.

TABLE II

Effects of Temperature on the Relative Rate of Hydrolysis of 2-Acetyl-1,2-bis(methylsulfonyl)-1-(2-chloroethyl)hydrazine

| Temperature, °C. | Relative rate of hydrolysis |
|---|---|
| 23 | 0.21 |
| 30 | 0.57 |
| 32 | 0.72 |
| 37 | 1.00 |

TABLE III

Effects of pH on the Relative Rate of Hydrolysis of 2-Acetyl-1,2-bis(methylsulfonyl)-1-(2-chloroethyl)hydrazine

| pH | Relative rate of hydrolysis |
|---|---|
| 7.4 | 0.48 |
| 7.5 | 0.57 |
| 7.6 | 0.70 |
| 7.8 | 1.00 |

EXAMPLE 14

To verify that the prodrugs would be converted to alkylating species in vivo, we performed studies on the kinetics of hydrolysis of these compounds in the presence of serum and also in the presence of proteinase K (a protease of low specificity). These studies indicated that both serum and proteinase K were capable of readily catalyzing this process. Serum from different sources, i.e., mouse, bovine and man, were not equivalent in their activities or in their rank order of substrate specificity. The two most sensitive compounds were the compounds of Examples 5 and 6 in all cases. Table IV reports the effects of bovine serum concentrates on hydrolysis of two compounds—the compounds of Example 1 and Example 6.

TABLE IV

Effects of Bovine Serum Concentration on the Rates of Hydrolysis of 2-Acetyl-1,2-bis(methylsulfonyl)-1-(2-chloroethyl)hydrazine (Example 1) and 2-Benzoyl-1,2-bis(methylsulfonyl)-1-(2-chloroethyl)hydrazine (Example 6)

| | Rate of hydrolysis[a] | |
|---|---|---|
| Serum concn., %, v/v | Compd 1 | Compd 6 |
| 0 | 0.02 | 0.06 |
| 5 | 0.055 | 0.22 |
| 10 | 0.10 | 0.52 |

TABLE IV-continued

Effects of Bovine Serum Concentration on the Rates of Hydrolysis of 2-Acetyl-1,2-bis(methylsulfonyl)-1-(2-chloroethyl)hydrazine (Example 1) and 2-Benzoyl-1,2-bis(methylsulfonyl)-1-(2-chloroethyl)hydrazine (Example 6)

| Serum concn., %, v/v | Rate of hydrolysis[a] | |
|---|---|---|
| | Compd 1 | Compd 6 |
| 20 | 0.26 | 1.31 |

[a]Expressed nmol/ml/min for a 200 μM solution.

Boiling dilute solutions of bovine serum decreased its ability to hydrolyze the compound of Example 1 by >75%, suggesting that serum proteins, possibly esterases and proteases, were important for this activity. The residual activity may be due to "non-denaturable" thiols present in the serum.

Serum was capable of stimulating the alkylation of the model nucleophile, 4-(4'-nitrobenzyl)pyridine, by 2-acyl-1,2-bis(methylsulfonyl)-1-(2-chloroethyl)hydrazines, providing direct evidence for the serum-dependent generation of the alkylating species from these prodrugs (Table V).

TABLE V

Relative Alkylation of 4-(4'-Nitrobenzyl)pyridine (NBP) by 4 mM 2-Acetyl-1,2-bis(methylsulfonyl)-1-(2-chloroethyl)hydrazine at 37° C. for 1 h in 100 mM Phosphate Buffer (pH 7.4) in the Presence and Absence of 20% Bovine Serum

| Conditions | Relative alkylation of NBP |
|---|---|
| No serum | 1.0 |
| Bovine serum (20%) | 5.7 |

EXAMPLE 15

Resistance to a large number of alkylating agents has been shown to be correlated with increased levels of glutathione (GSH) and glutathione-S-transferase (GST) enzymes (see Stewart and Evans (1989) *Cancer Treat. Rep.* 16:1–40), suggesting that the protective effect afforded by elevated non-protein thiol levels could be due to a direct interaction between the sulfhydryl and the electrophilic alkylating species. Buthionine sulfoximine has been shown to reverse this resistance by reducing cellular GSH levels and to increase the in vitro cytotoxicity and in vivo anticancer activity of a variety of alkylating agents, such as cyclophosphamide, melphalan and the nitrosoureas. Stewart and Evans, cited above. Furthermore, many neoplastic cell lines, which have not been subjected to drug selection pressures have intrinsically high levels of GSH. Penketh et al., cited above. The resistance of these cell lines to various therapeutic strategies has been attributed to their high non-protein thiol and GST contents.

If the process of activating the prodrugs of the invention involves consumption of free thiols, the protective effect afforded by non-protein sulfhydryls would also be minimized. Without wishing to bind ourselves to a specific mechanism, we believe that the removal of the acyl group from 2-acyl-1-alkyl-1,2-bis(methylsulfonyl)-hydrazines can proceed not only by hydrolytic cleavage of the N-acyl bond, but also via nucleophilic attack of the carbonyl carbon by a sulfur-containing nucleophile, according to the following scheme.

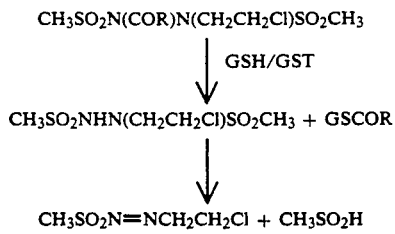

Our belief is confirmed by the following experiment in which we incubated a solution of 2-benzoyl-1,2-bis(methylsulfonyl)-1-methylhydrazine ($R=C_6H_5$) in phosphate buffer (pH 7.4) at 37° C. in the presence and absence of GSH. The amount of methanol generated in 10 min, determined using alcohol oxidase by methodology described by Penketh et al. (1990) 33:730–732, was used as a measure of activation of the prodrug. In the presence of 1 mM GSH, the amount of methanol generated increased approximately 10-fold, relative to that occurring in phosphate buffer alone. Subsequent experiments showed that the rate of activation of the prodrug was directly proportional to the GSH concentration, suggesting that the rate of generation of the alkylating species from the above compound is much faster than the rate of reaction of the alkylating species with GSH. Similar results, but of smaller magnitude, were obtained with the 2-acetyl analog. In the case of the 1-(2-chloroethyl) derivative (the compound of Example 6), 22although precise quantitation was difficult due to the limitations of the assay, the compound of Example 6 gave a 6- to 7-fold greater amount of alkylated product when reacted with the nucleophile 4-(4'-nitrobenyl)-pyridine in the presence of 5 mM GSH for 30 min at 37° C. than in its absence.

Therefore, tumors resistant to conventional chloroethylating agents because of the protective effect conferred by high levels of intracellular thiols, may be more sensitive to 2-acyl-1,2-bis(methylsulfonyl)-1-methyl (or 2-chloroethyl)hydrazines. Moreover, we have found that the GSH activation of the prodrug derivative where $R=C_6H_5$ can be catalyzed by GST (13.5 units/ml of equine liver enzyme as determined by the 1-chloro-2,4-dinitrobenzene assay), doubling the activation rate. Although elevation of GST levels has been associated with increased resistance to a variety of alkylating agents, such a change is expected to increase sensitivity to the thiol-activated prodrugs.

Other embodiments are within the following claims. We claim:

1. A composition of matter comprising a compound having the formula

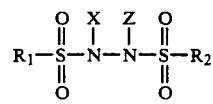

where $R_1$ and $R_2$ are; X is

and $R_3$ is $-CH_3$, $-C_2H_5$, $-n-C_3H_7$, $t-C(CH_3)_3$, $-CH_2-O-CH_3$, or $-C_6H_5$; and Z is $-CH_3$ or $-CH_2CH_2Y$, where Y is a halo group.

2. The composition of claim 1 in which Y is a chloro group.

3. The composition of claim 1 in which each of $R_1$ and $R_2$ (independently) is a methyl or ethyl group, and Z is a methyl or 2-chloroethyl group.

4. The composition of claim 1 in which $R_1$ and $R_2$ are —$CH_3$, Z is —$CH_2CH_2Cl$, and X is —$CO$—$C_2H_5$.

5. The composition of claim 1 in which $R_1$ and $R_2$ are —$CH_3$, Z is —$CH_2CH_2Cl$, and X is —$CO$—n—$C_3H_7$.

6. The composition of claim 1 in which $R_1$ and $R_2$ are —$CH_3$, Z is —$CH_2CH_2Cl$, and X is —$CO$—$C(CH_3)_3$.

7. The composition of claim 1 in which $R_1$ and $R_2$ are —$CH_3$, Z is —$CH_2CH_2Cl$, and X is —$CO$—$CH_2$—$O$—$CH_3$.

8. The composition of claim 1 in which $R_1$ and $R_2$ are —$CH_3$, Z is —$CH_2CH_2Cl$, and X is —$CO$—$C_6H_5$.

9. The composition:

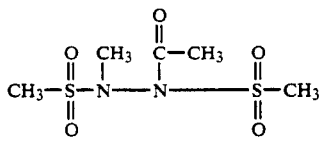

10. The composition:

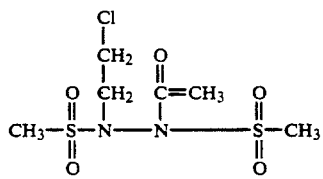

11. A method for controlling neoplastic cell growth comprising administering the compound of any one of claims 1-10 to said cells.

12. The method of claim 11 in which said compound is administered to a non-human mammal.

13. The method of claim 11 in which said compound is administered to a human patient.

14. The method of claim 11 in which said compound is administered to cells cultured in vitro.

* * * * *

UNITED STATES PATENT AND TRADEMARK OFFICE
CERTIFICATE OF CORRECTION

PATENT NO. : 5,256,820

DATED : October 26, 1993

INVENTOR(S) : Alan C. Sartorelli et al.

It is certified that error appears in the above-identified patent and that said Letters Patent is hereby corrected as shown below:

On the title page, item [56] References Cited:
In Other Publications, the first publication (Shyam et al.), "trypanocidal" should be --Trypanocidal--.

In the Abstract, line 2, "hydrazine" should be --hydrazines--.

Column 2, lines 17-18, add --protease-mediated-- before "hydrolytic".

Column 2, line 26, "water soluble" should be --water-soluble--.

Column 4, line 26, "in" should be --to--.

Column 6, line 8, "compounds" should be --compound--.

Column 6, line 56, "concentrates" should be --concentration--.

Column 7, line 10, insert --as-- after "Expressed".

Column 8, line 30, delete "22" before "al-".

Column 8, line 60, insert --are each independently methyl or ethyl-- after "are".

Column 9, line 21, "-CH" should be ---$CH_2$--, and delete "2" on the following line.

UNITED STATES PATENT AND TRADEMARK OFFICE
CERTIFICATE OF CORRECTION

PATENT NO. : 5,256,820

DATED : October 26, 1993

INVENTOR(S) : Alan C. Sartorelli et al

It is certified that error appears in the above-indentified patent and that said Letters Patent is hereby corrected as shown below:

Column 10, line 14, "$=CH_3$" should be ---$CH_3$---.

Signed and Sealed this

Twentieth Day of September, 1994

Attest:

BRUCE LEHMAN

Attesting Officer

Commissioner of Patents and Trademarks